United States Patent [19]

Muraoka et al.

[11] Patent Number: 5,643,404
[45] Date of Patent: Jul. 1, 1997

[54] METHOD FOR EXAMINATION OF SILICON WAFER SURFACE DEFECTS

[75] Inventors: Hisashi Muraoka; Yuji Fukazawa, both of Yokohama, Japan

[73] Assignees: Purex Co., Ltd.; Kabushiki Kaisha Toshiba, both of Japan

[21] Appl. No.: 529,603

[22] Filed: Sep. 18, 1995

[30] Foreign Application Priority Data

Sep. 16, 1994 [JP] Japan .................................. 6-259901

[51] Int. Cl.⁶ .................................................. H01L 21/00
[52] U.S. Cl. .................................... 156/626.1; 156/628.1; 156/662.1; 216/87
[58] Field of Search ........................... 156/626.1, 628.1, 156/662.1; 437/8; 216/87, 55

[56] References Cited

U.S. PATENT DOCUMENTS 3,518,131  6/1970  Glendinning .

*Primary Examiner*—William Powell
*Attorney, Agent, or Firm*—Wenderoth, Lind & Ponack

[57] ABSTRACT

A method of examining surface defects of silicon wafer surfaces, comprising (A) preparing a semiconductor treating solution containing an impurity element labelled with a radioactive isotope; (B) bringing a silicon wafer whose crystal surface is laid bare, into contact with the treating solution to obtain a specimen wafer on which the labelled impurity has been adsorbed; (C) recording in a photostimulable phosphor layer a data of radioactivity intensible distribution present in the surface of the specimen wafer; the pattern being recorded as a latent image; and (D) reading as a visual image the data of radioactivity intensity distribution recorded in the photostimulable phosphor layer, to observe the radioactivity intensity distribution shown on the image, whereby the distribution of the surface defects being detected. It is possible to catch at a glance as a visual image the extent and distribution of the surface defects including crystal defects and surface states formed by contamination with impurities and to make easy the evaluation of silicon wafers.

9 Claims, 2 Drawing Sheets

METHOD FOR EXAMINATION OF SILICON WAFER SURFACE DEFECTS

BACKGROUND OF THE INVENTION

1. Field of the Invention

This invention relates to a method of examining the extent and distribution of surface defects including crystal defects and contamination with impurities of silicon wafers, which occur in the process of manufacturing semiconductor silicon wafers and in the process of fabricating silicon devices by processing the semiconductor silicon wafers.

2. Description of the Prior Art

In the process of fabricating silicon devices, it is well known that deterioration occur when crystal defects are present in the device active areas of silicon wafers.

In the process of fabricating silicon devices, it is well known that, when silicon wafers are heat-treated, harmful impurity metal elements are attracted to crystal defects to precipitate thereto. As a technique utilizing such phenomenon, gettering is known in the art, according to which crystal defects are formed intentionally in the area other than the device active area in a silicon wafer surface and impurity metal elements are collected thereto. However, if crystal defects are present in the silicon wafer surface, the impurity metal elements precipitate to the crystal defects and are trapped to make resulting devices deteriorative. The extent to which the impurity metal elements are trapped by such crystal defects differs depending on the type or state of crystal defects or the type of impurity metal elements. Usually, the impurity metal elements that may be trapped in crystal defects and are harmful in the process of fabricating silicon devices in semiconductor factories are typified by heavy metals such as Cu, Fe and Ni, and alkali metals and alkaline earth metals such as Na and Ca. Hence, such impurity metal elements are main targets for making clean the silicon device fabrication process.

Hence, the examination of crystal defects in silicon wafer surfaces is an important item in surface evaluation of semiconductors. As typical examination methods, there is, e.g., a method in which, utilizing the tendency that etching reaction locally takes place at crystal defects in the surfaces, the crystal defects in silicon wafers are actualized by selective etching so that the defects can be observed by a microscope. It is also common to use an electron microscope to directly observe the areas having crystal defects in the surface. As a method of directly observing disorders of crystal lattices, there is a method in which X-ray diffraction is utilized, such as X-ray lang's method. It is also attempted to use a method in which light is projected on silicon wafer surfaces and its reflectance or complex refractive index spectra are measured to examine the crystal defects in the surfaces.

Most of these examination methods, however, are suited for the examination of crystal defects microscopically or locally present in the silicon wafer surfaces, and many of them are not suitable for catching the whole distribution of crystal defects in silicon wafer surfaces. For example, in the above examination method making use of etching, the distribution of crystal defects in the whole silicon wafer surface can not be observed with the naked eye except the case when any lineage, strong structural defects, appear to the silicon wafer surfaces or when a large quantity of dislocation or micro-defects appear in a haze. Also, the X-ray lang's method using X-ray diffraction is suited for the examination of structural defects such as dislocation and layer defects and enables photographic observation of the distribution of such structural defects of the whole silicon wafer surface, but is not effective as an examination method for amorphously damaged or cluster of point defects like the defects caused by ion implantation.

Furthermore, the examination methods described above can not examine contamination with impurities which can absorb on areas having no crystal defects and may form surface states.

SUMMARY OF THE INVENTION

An object of the present invention is to provide an examination method for surface defects of silicon wafers surfaces including crystal defects and contamination thereon, that can catch at a glance as a visual image the extent and distribution of all the surface defects, that trap harmful impurity elements to be removed for making clean in the silicon device fabrication process, and also can quantitatively show the extent of surface defects.

The present invention provides a method of examining surface defects of silicon wafers, comprising;

(A) preparing a semiconductor treating solution containing an impurity element harmful in the process of manufacturing semiconductors; the impurity elements having been labelled with a radioactive isotope;

(B) bringing a silicon wafer whose surface is laid bare, into contact with the semiconductor treating solution to obtain a harmful-element adsorbed wafer on which the labelled impurity element has been adsorbed;

(C) recording in a photostimulable phosphor layer a data of radioactivity intensity distribution present in the surface of the harmful-element adsorbed wafer; the pattern being recorded as a latent image; and (D) reading as a visual image the data of radioactivity intensity distribution recorded in the photostimulable phosphor layer, to observe the radioactivity intensity distribution shown on the image, whereby the distribution of the surface defects being detected.

The examination method of the present invention makes it possible to catch at a glance the extent and distribution of surface defects in the whole silicon wafer by comparing the difference in density of absorbed impurity elements in the area where little surface defects are present density and the area where many surface defects are present; the difference being shown as a visual image. This has been impossible in the conventional, whole surface crystal defect examination methods utilizing etching or X-ray diffraction. The extent of surface defects can also be quantitatively examined. In the process of manufacturing silicon devices, a high practical utility can be promised in respect of management such as maintenance of yield of silicon devices, because the present method can be directly applied to analysis of defective wafers by examining the surface defects in relation to the power to trap harmful impurity elements which directly cause defectives.

DESCRIPTION OF THE PREFERRED EMBODIMENTS

Figure 1:
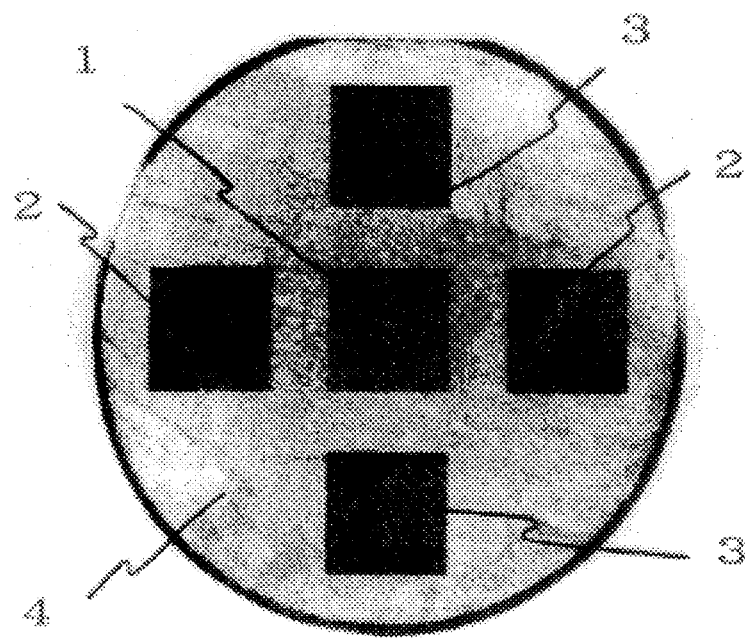
FIG. 1 is a photograph taken in Example 1 by photographing an image formed by reading on an imaging analyzer BAS2000 the radioactivity intensity distribution of a wafer, recorded in an imaging plate.

The present invention will be described below in detail.

The surface defects is herein meant to include crystal defects in the surface of the silicon wafer and surface states formed by contamination with impurities. The crystal defects include cluster of point defects such as vacancy, interstitial impurity and substitutional impurity, line defects like various dislocations, face defects such as grain boundary, twin and stacking fault, amorphously damaged area, and micro-roughness which may cause haiz. The impurities causing the contamination include impurity elements, e.g., heavy metals such as Fe, Cu, Ni and Au, alkalimetals such as Na and alkaline earth metals such as Ca and Mg, and various organic matter.

Step (A)

In the present invention, first, the impurity element harmful in the process of manufacturing semiconductors is labelled with a radioactive isotope and the labelled impurity element is added to a semiconductor treating solution. Thus, a semiconductor treating solution containing the labelled impurity element is prepared.

The radioactive isotope used in the present invention includes $^{64}Cu$, $^{61}Cu$, $^{59}Fe$, $^{57}Ni$, $^{22}Na$, $^{24}Na$, $^{45}Ca$, $^{198}Au$ and so forth, corresponding to Cu, Fe, Ni, Na, Ca and Au which are typical impurity elements harmful in the process of manufacturing semiconductors. Also, when, for example, silicon wafers are immersed in a treating solution containing hydrofluoric acid, the adsorption of fluorine (F), a major element of the solution, on the wafer surface is accelerated by the surface defects. Since F ions have a strong activity on $SiO_2$ films necessary for device structures, there is a possibility that the resulting devices turn out defective. Thus, in the examination method of the present invention, non-metallic radioactive elements such as $^{18}F$ can be included in the radioactive isotopes.

The semiconductor treating solution used in the present invention may preferably be a solution commonly in wide use in actual processes of manufacturing semiconductors, including, e.g., an ammonia/hydrogen peroxide cleaner (hereinafter "SC-1"), a hydrochloric acid/hydrogen peroxide cleaner (hereinafter "SC-2"), and hydrofluoric acid-containing treating solutions such as diluted hydrofluoric acid and ammonium fluoride buffered hydrofluoric acid. In particular, the hydrofluoric acid-containing treating solutions are suited for examination methods making use of $^{64}Cu$, $^{61}Cu$, $^{198}Au$ or $^{18}F$ as a label. The SC-1 is suited for examination methods making use of $^{59}Fe$ as a label. An impurity element described above may be added to the semiconductor treating solution in an appropriate form depending on the impurity element, e.g. in the form of a water-soluble salt in the case of a metal, e.g., in the form of a chloride, an acetate or a nitrate.

In the case of metal impurities such as Cu, Fe, or the like, the impurity element labelled with a radioactive isotope may be added in the semiconductor treating solution in an amount of from about 0.1 ppb to about 10 ppb based on the semiconductor treating solution. In the case of $^{18}F$, an aqueous solution containing hydrofluoric acid in a concentration of 10 to 1,000 ppm in pure water, added with $^{18}F$ so as to have a radioactivity of about 1,000 Bq/ml.

Step (B)

A silicon wafer whose crystal surface is laid bare is brought into contact with, e.g., immersed in, the above semiconductor treating solution to obtain a harmful-element adsorbed wafer (hereinafter simply referred to specimen) on which the labelled impurity element has been adsorbed. In the case when the silicon wafer is a starting material of a silicon device, the silicon wafer may preferably be subjected to heat treatment before the impurity element is adsorbed thereon, and may particularly preferably be subjected to thermal oxidation in an oxidizing atmosphere. Such heat treatment of the silicon wafer can actualize any latent defects in silicon crystals as defects on the surface of the silicon wafer. Then, if the adsorption of the impurity element labelled with a radioactive isotope on the actualized portions in the wafer surface is accelerated as compared with on portions having less defects, the effect on the wafer surface of crystal defects caused during the manufacture of single crystals can also be found.

In the case when the silicon wafer subjected to the thermal oxidation is used, the oxide film produced on the surface of the silicon wafer must be removed by hydrofluoric acid or the like before it is brought into contact with the semiconductor treating solution.

In the case when the impurity element to be trapped in crystal defects in the surfaces of a silicon wafer is Cu and the treating solution in which the silicon wafer is immersed is a hydrofluoric acid-containing solution, the adsorption of Cu on the surface of the silicon wafer may be greatly affected by organic matter having adhered onto the silicon wafer. Hence, in the examination of the surface crystal defects of such a silicon wafer, the organic matter having adhered to the wafer surface may preferably be previously removed by exposing the wafer to ultraviolet rays so that the organic matter is decomposed by the ozone generated, or by cleaning the wafer with SC-1. Previously removing the organic matter in this way makes it possible to effect the examination of the distribution of the crystal defects in the surface of the silicon wafer, independently of the effect of the surface states formed by the adsorption of the organic matter, and also to improve reproducibility in the examination method of the present invention.

Figure 2:
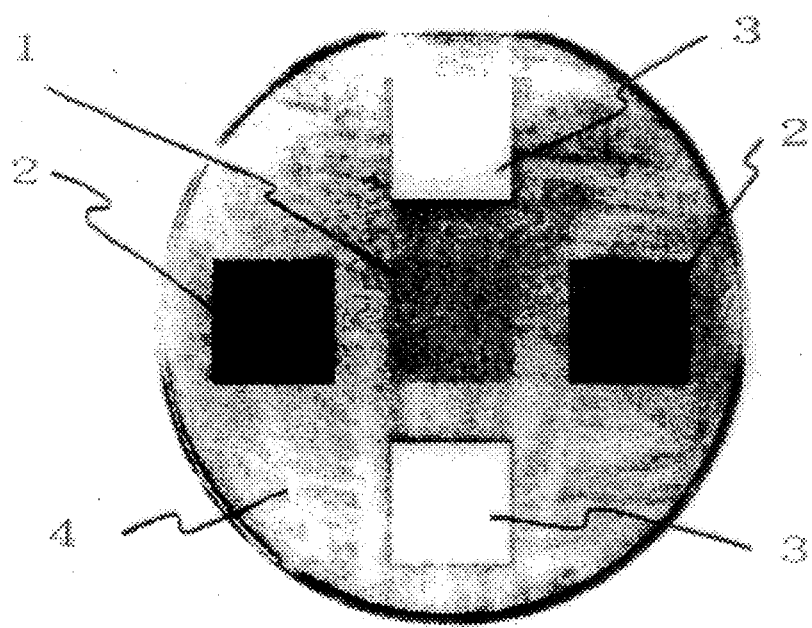
FIG. 2 is a photograph taken in Example 2 by photographing an image formed by reading on an imaging analyzer BAS2000 the radioactivity intensity distribution of a wafer, recorded in an imaging plate.
Figure 3:
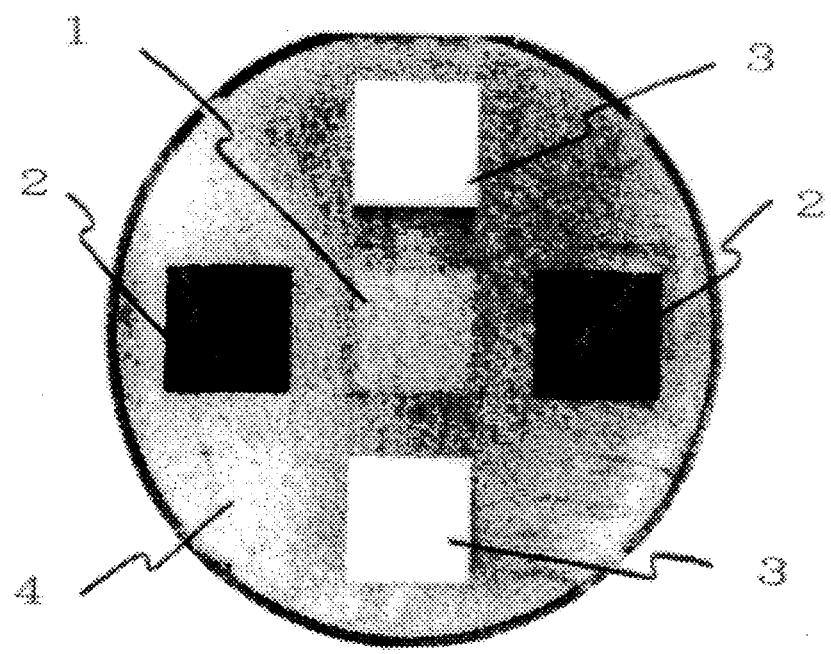
FIG. 3 is a photograph taken in Example 3 by photographing an image formed by reading on an imaging analyzer BAS2000 the radioactivity intensity distribution of a wafer, recorded in an imaging plate.

If, on the other hand, the step (B) is carried out without removing the organic matter, the status of harmful surface states formed by the organic matter can be examined simultaneously (see the area 4 in FIGS. 1, 2 and 3).

The surface of silicon wafers on the process of manufacturing devices are generally subjected to organic contamination caused by adsorption of organic gas impurities contained in the air in a clean room or generated in the production equipments. When a silicon wafer is immersed in a radioactive Cu-added hydrofluoric acid, the contamination of same organic matters accelerates the adsorption of the Cu onto the silicon wafer. Since the adsorption of organic matter on a silicon wafer does not occur uniformly, Cu adsorbs onto the silicon wafer irregularly. Therefore, immersion of a silicon wafer as described above makes it possible to examine not only the distribution of crystal defects in the surface of the silicon wafer but also the distribution of contamination with organic matters on the surface including areas having no or little crystal defects simultaneously.

In the examination method of the present invention, after the specimen has been obtained as described above, a cleaning treatment to remove the greater part (at least 80%, specifically 80–95%) of the radioactive isotope adsorbed on the specimen may preferably be applied before the next step (C) is carried out.

As a cleaning solution used in the cleaning to remove the greater part of the radioactive isotope, the SC-1 or SC-2 commonly used in semiconductor manufacturing processes may be well used. As a result of such cleaning, the difference in density between an area having less surface defects and an area where many surface defects are present can be greatly strengthened in the visual image that represents radioactivity intensity distribution as described later. Hence, it becomes easy to compare the extent of surface defects, and it is possible to clearly catch the extent to which the surface defects trap specific impurity elements, so that the distribution of surface defects can be confirmed with ease.

Step (C)

In this step, the pattern of radioactivity intensity distribution present in the surface of the specimen is recorded as a latent image in a photostimulable phosphor layer.

The steps (C) and (D) described below apply computed radiography (CR) (also called digital radiography by imaging plate) which is already established as a medical diagnostic technique.

The "photostimulable phosphor" refers to a fluorescent substance in which radiation energy is accumulated upon exposure to radiation and which, upon exposure to visible light thereafter, is again excited to generate photostimulated fluorescence (PSF) with a short lifetime, the intensity of which is proportional to that of the radiation initially applied. Such a photostimulable phosphor is known to include, e.g., halogenated barium fluorides (typically BaFBr) doped with $Eu^{2+}$.

When there is an intensity distribution in the radiation to which the fluorescent substance has been exposed, a latent image (i.e., distribution of accumulated energy) corresponding to the distribution is formed in the fluorescent substance. Upon exposure of the fluorescent substance to red light, the substance is again excited to generate blue PSF the intensity of which is proportional to that of the radiation initially applied. Since this fluorescence has a short lifetime, the substance is scanned with red light by means of a reader and the amount of photostimulated fluorescence is calibrated using a photoelectron multiplier, whereby the latent image can be converted to a visual image. A product comprising a substrate made of polyester and a photostimulable phosphor layer formed thereon is known as an imaging plate (IP), and is commercially available from Fuji Photo Film Co., Ltd.

In this step (C), the photostimulable phosphor layer of the imaging plate is brought into close contact with the surface of the specimen and the resulting wafer is exposed to light, whereupon the intensity distribution of the radioactive isotope in the surface of the wafer is recorded as a latent image in the photostimulable phosphor layer.

Step (D)

In this step, the data of radioactivity intensity distribution recorded in the photostimulable phosphor layer are read as a visual image (a display image), and the radioactivity intensity distribution in the surface of the harmful-element adsorbed sample, shown on the visual image is observed. Stated specifically, radioactivity intensities at the portions corresponding to an area having a good surface state (i.e., the area having no or little surface defects) and the area where many surface defects are present are compared.

The radioactivity intensity distribution in the surface of specimen, recorded in the photostimulable phosphor layer, is read by scanning the surface of the photostimulable phosphor layer with a red-color laser. This scanning with the laser causes emission (photostimulated fluorescence) of blue color in proportion to the amount of radiations recorded (the latent image). Thus, this blue light is separated by a color filter to make measurement, whereby the radioactivity intensity distribution in the surface of the harmful-element adsorbed sample can be seen.

For example, when an imaging analyzer BAS2000, available from Fuji Photo Film Co., Ltd. is used, the emitted blue color is converted to electric signals and once recorded in a magnetic disk. The recorded data are then converted to a display image on a cathode-ray tube screen of the analyzer. Namely, the intensity distribution of the radiolabelled elements present in the surface of the specimen is obtained as a display image. On the display image, the area where radioactivity intensity (in BAS2000, indicated as a relative unit called PSL) is specified to carry out analysis automatically, and the radioactivity intensity in the specified area is, after a background PSL value (indicated as BG) is subtracted therefrom, displayed on the screen as an intensity (PSL-BG) per 1 $mm^2$. A standard specimen wafer containing a known amount of the like radioactive isotope is exposed to light at the same time the specimen is. Thus, the elemental density in a specified area in the harmful-element adsorbed sample can be quantitatively determined by its comparison with the PSL-BG value of the standard specimen.

The examination method of the present invention is based on the fact that the impurity element is adsorbed in a larger quantity in the area having surface defects than in the area having no or less crystal defects, and the radioactivity intensities at the portions corresponding to the area having a good surface state and the area where many surface defects are present, in the surface of the harmful-element adsorbed sample are compared. Thus, the extent and distribution of the surface defects can be examined.

EXAMPLES

The present invention will be described below in greater detail by giving Examples. The present invention is by no means limited to these Examples. The present invention is a method of examining surface defects of silicon wafer surfaces, which occur in the process of manufacturing semiconductor silicon wafers or in the process of fabricating silicon devices by processing the semiconductor silicon wafers. This examination method is useful for the management of the process of manufacturing semiconductors. Hence, it is preferable to present Examples in which the examination is made on surface defects which occur in an actual process of manufacturing semiconductors. However, with regard to the surface defects occurring in the process of manufacturing silicon devices to which the present invention is especially effectively applicable, the device structure is so fine and complicated that it is difficult to specifically describe the present invention. Accordingly, in the present Examples, test wafers prepared by simulating the course of occurrence of surface defects in an actual manufacturing process are used to describe the present invention in greater detail.

Example 1

By a lithographic process commonly used in the manufacture of semiconductors, a test silicon wafer (n-type) with selectively ion-implanted square areas 1 to 3 as shown in FIG. 1 was prepared. In the areas 1, 2 and 3, Ar, As and B (using $BF^{2+}$ ions) had been ion-implanted, respectively, in the same doses ($5 \times 10^{14}$ ions/$cm^2$). In these areas 1 to 3, known defects caused by ion implantation had occurred. Area 4 was an area where no ion implantation had been applied, having a good crystalline state or having no or little surface defects.

This test wafer was immersed for 10 minutes in a solution of ammonium fluoride buffered hydrofluoric acid to which 0.5 ppb of Cu labelled with $^{64}$Cu was added. Subsequently, this test wafer was drawn up, and rinsed with pure water for 5 minutes, followed by drying to obtain a harmful-element adsorbed sample.

Next, the harmful-element adsorbed sample and an imaging plate (available from Fuji Photo Film Co.,Ltd.) was put together so that the former's side having the areas 1 to 4 came into close contact with the latter's side having the photostimulable phosphor layer. Thus the imaging plate being exposed to radiation.

Next, the radioactivity intensity distribution of the wafer, recorded in the imaging plate thus exposed, was read on the imaging analyzer BAS2000. The image formed here in the imaging plate is shown in FIG. 1. In FIG. 1, the more densely an area looks black, the greater the Cu adsorption quantity is. The $^{64}$Cu densities in the areas 1 to 4 were also determined by comparing PSL measured using the imaging analyzer BAS2000 with PSL of the standard specimen sample having the known Cu density. As the result, the $^{64}$Cu densities in the areas 1 to 3 were $3.6 \times 10^{11}$ atoms/cm$^2$ in the area 1, Ar-implanted area, $3.7 \times 10^{11}$ atoms/cm$^2$ in the area 2, As-implanted area, and $3.7 \times 10^{11}$ atoms/cm$^2$ in the area 3, B-implanted area. The $^{64}$Cu density in the area 4, having no defects caused by ion implantation, was $2.0 \times 10^{11}$ atoms/cm$^2$, which was distinctly less than the $^{64}$Cu densities in the areas 1 to 3. According to the present invention, the comparison of difference in density between the area having a comparatively good surface state and the area where more crystal defects are present makes it possible to catch and quantitatively examine the extent and distribution of surface defects in the whole silicon wafer surface.

As also seen in other figures, adsorption of $^{14}$Cu is also observed on the areas having a good crystalline status. These areas were presumably contaminated with organic matter as described later in Example 7 to form surface states, which act as crystal defects and affect the adsorption of $^{64}$Cu.

Example 2

In the actual process of manufacturing silicon devices, silicon wafers are always heated (annealed) after ion implantation in order to remove the defects caused by the ion implantation. To confirm how far the defects have been removed, it is prevalent to measure electrical conductivity of the ion-implanted areas to examine the degree of dopant activation. Now, a test wafer prepared in the same manner as in Example 1 was annealed at 900° C., which was the condition under which removal of defects could be confirmed.

Next, a harmful-element adsorbed sample was prepared in the same manner as in Example 1 except for using this test wafer. An imaging plate similarly prepared using this harmful-element adsorbed sample was exposed to radiation, and the radioactivity intensity distribution of the harmful-element adsorbed sample, recorded in the imaging plate thus exposed, was read on the imaging analyzer BAS2000 in the same manner as in Example 1. The image formed here in the imaging plate is shown in FIG. 2. The $^{64}$Cu densities in the areas 1 to 4 were measured in the same manner as in Example 1. As the result, the $^{64}$Cu density was $2.7 \times 10^{11}$ atoms/cm$^2$ in the area 1, Ar-implanted area, $3.3 \times 10^{11}$ atoms/cm$^2$ in the area 2, As-implanted area, and $3.9 \times 10^{10}$ atoms/cm$^2$ in the area 3, B-implanted area. The $^{64}$Cu density in the area 4, having no defects caused by ion implantation, was $2.3 \times 10^{11}$ atoms/cm$^2$.

So far as the measurements of electrical conductivity stated above are studied, the defects caused by ion implantation should have been substantially disappeared on account of the above annealing. However, as a result of the examination of surface defects in the present Example, it was possible to confirm that the defects participating in the trap of Cu had fairly remained in the As-implanted area 2 and the Ar-implanted area 1. Meanwhile, in the B-implanted area 3, the $^{64}$Cu density had decreased by about one figure compared with the non-implanted area 4. This is presumably because defects of the type capable of decelerating the adsorption of Cu were present in the wafer surface.

Example 3

A test wafer was prepared in the same manner as in Example 1 except that the n-type test silicon wafer was replaced with a p-type silicon wafer and the Ar, As and B were ion-implanted in a dose made smaller by one figure. Then, a harmful-element adsorbed sample was prepared in the same manner as in Example 1 except for using this test wafer. An imaging plate similarly prepared using this harmful-element adsorbed sample was exposed to radiation, and the radioactivity intensity distribution of the harmful-element adsorbed sample, recorded in the imaging plate thus exposed, was read on the imaging analyzer BAS2000. The image formed here in the imaging plate is shown in FIG. 3. The $^{64}$Cu densities in the areas 1 to 4 were measured in the same manner as in Example 1. As the result, the $^{64}$Cu density was $2.2 \times 10^{11}$ atoms/cm$^2$ in the area 1, Ar-implanted area, $3.2 \times 10^{11}$ atoms/cm$^2$ in the area 2, As-implanted area, and $1.9 \times 10^{11}$ atoms/cm$^2$ in the area 3, B-implanted area. The $^{64}$Cu density in the area 4, having no defects caused by ion implantation, was $2.3 \times 10^{11}$ atoms/cm$^2$.

In the case when the ion implantation was carried out using the p-type silicon wafer and in a dose of $5 \times 10^{13}$ ions/cm$^2$, the adsorption of Cu is seen to be accelerated only in the As-implanted area, whereas in the B-implanted area 3 the defects of Cu adsorption decelerating type are presumed to exist in the wafer surface.

Example 4

A test wafer was prepared in the same manner as in Example 3. Then, this wafer was annealed at 900° C. in order to decrease the defects caused by ion implantation to the wafer.

Next, a harmful-element adsorbed sample was prepared in the same manner as in Example 3 except for using this test wafer. An imaging plate similarly prepared using this harmful-element adsorbed sample was exposed to radiation, and the radioactivity intensity distribution of the harmful-element adsorbed sample, recorded in the imaging plate thus exposed, was read on the imaging analyzer BAS2000. The $^{64}$Cu densities in the areas 1 to 4 were measured in the same manner as in Example 1 to obtain measurements little different from those in Example 3.

The results suggest that since in Examples 3 and 4 the amount of implaneted ions was small, the effect of annealing was small.

Example 5

A harmful-element adsorbed sample was prepared in the same manner as in Example 1, and the sample was cleaned for 10 minutes using the 70° C. SC-1 (NH$_4$OH:H$_2$O$_2$:H$_2$O=

1:1:5 (by volume). An imaging plate was exposed to radiation in the same manner as in Example 1 except that the harmful-element adsorbed sample used therein was replaced with the above cleaned harmful-element adsorbed sample. The radioactivity intensity distribution of the harmful-element adsorbed sample, recorded in the imaging plate thus exposed, was read on the imaging analyzer BAS2000. Then the $^{64}$Cu densities in the areas 1 to 4 were measured in the same manner as in Example 1. Results obtained are shown in Table 1.

Example 6

A harmful-element adsorbed sample was prepared in the same manner as in Example 2, and the sample was cleaned for 10 minutes using the SC-1 as in Example 5. An imaging plate was exposed to radiation in the same manner as in Example 2 except that the harmful-element adsorbed sample used therein was replaced with the above cleaned harmful-element adsorbed sample. The radioactivity intensity distribution of the harmful-element adsorbed sample, recorded in the imaging plate thus exposed, was read on the imaging analyzer BAS2000. Then the $^{64}$Cu densities in the areas 1 to 4 were measured in the same manner as in Example 1. Results obtained are shown in Table 1.

TABLE 2

| | $^{64}$Cu density ($\times 10^{10}$ atoms/cm$^2$) | | | |
|---|---|---|---|---|
| Example | Ar ion-implanted area 1 | As ion-implanted area 2 | B ion-implanted area 3 | Non implanted area 1 |
| 1 | 36 | 37 | 37 | 20 |
| 5 (Ex. 1 + SC-1) | 39 | 37 | 42 | 0.12 |
| 2 (annealing) | 27 | 33 | 3.9 | 23 |
| 6 (Ex. 2 + SC-1) | 7.6 | <0.12 | 3.1 | <0.12 |

As is seen from Table 1, in Examples 1 and 2 the ratio of $^{64}$Cu densities in the ion-implanted areas 1 to 3 to $^{64}$Cu density in the non-implanted area 4 (the adsorption quantity ratio) is approximately 1.8 to 1.2 (36/20 to 27/23) (except for the B-implanted area 3 in Example 2 where the wafer was annealed at 900° C.). On the other hand, in the case when the wafer was cleaned as in Examples 5 and 6, the above adsorption quantity ratio comes to exceed 30 times except for the As-implanted area in Example 6 which was annealed at 900° C. and become easy to reach with SC-1, and the difference in density can be made very greater, so that the crystal defects can be examined with ease.

Example 7

In experiments, it has become clear that the $^{64}$Cu adsorption quantity greatly increases when a container made of polypropylene is used as the container of the semiconductor treating solution in which the silicon wafers are immersed and when the silicon wafers drawn up therefrom are not well cleaned. This has been found to be caused by stearic acid soap which is an additive to plastics. As a result of studies further made, it has become clear that the $^{64}$Cu adsorption is similarly accelerated when the surface of the silicon wafer is contaminated with organic matter like stearic acid or a machine oil. The accelaration of Cu adsorption is presumed to be caused by surface states formed by the contamination with the organic matter.

Such an abnormal phenomenon was not seen at all in Examples 5 and 6 where the silicon wafers were cleaned with SC-1 having a strong cleaning power against organic contaminants on their surfaces. Now, in experiments, test wafers prepared were exposed to ultraviolet rays with wavelengthes of 184.9 nm and 253.7 nm so that possible organic matter was decomposed and removed by the ozone generated. Then, the test wafers were immersed and treated in a fluorocarbon polymer container. As a result, the reproducibility of $^{64}$Cu adsorption was remarkably improved and it became easy to examine crystal defects, in the wafer surfaces.

Example 8

A lithographic process was applied to an oxide film formed on a silicon wafer so that the oxide film was removed in parallel crosses at intervals of 5 mm to provide silicon crystal bared areas. Then, using the remaining oxide film as a mask, reactive etching was carried out to form 0.5 μm deep parallel-cross grooves in the silicon wafer surface. Next, the oxide film was removed using hydrofluoric acid to obtain a test wafer made to have a silicon crystal surface on the whole silicon wafer surface. Next, this test wafer was immersed for 3 minutes in a solution prepared by adding to an aqueous 1:100 dilute hydrofluoric acid solution 0.5 ppb of Cu labelled with $^{64}$Cu. Subsequently, this test wafer was drawn up, and rinsed with pure water for 5 minutes, followed by drying to obtain a harmful-element adsorbed sample.

An imaging plate was exposed to radiation in the same manner as in Example 1 except that the harmful-element adsorbed sample used therein was replaced with the harmful-element adsorbed sample of the present Example. The radioactivity intensity distribution of the harmful-element adsorbed sample, recorded in the imaging plate thus exposed, was read on the imaging analyzer BAS2000. Then the $^{64}$Cu densities in the area having crystal defects in the wafer surface caused by reactive etching and the non-etched area having a good surface state were determined by comparing PSL measured using the imaging analyzer BAS2000 with PSL of the standard sample having the known Cu density. As the result, the $^{64}$Cu density in the area having crystal defects was $1 \times 10^{11}$ atoms/cm$^2$, whereas the $^{64}$Cu density in the non-etched area was about $(7 \text{ to } 8) \times 10^9$ atoms/cm$^2$. Thus, the crystal defects can be examined with ease by comparing these $^{64}$Cu densities.

Example 9

By a lithographic process commonly used in the manufacture of semiconductors, a large number of As ion-implanted areas (1 cm×1 cm) were selectively formed in the surface of a silicon wafer (n-type). The ion implantation was carried out in substantially the same dose as in Example 1. Next, this test wafer was immersed for 10 minutes in a solution at 70° C. prepared by adding to the dilute cleaner SC-1 (NH$_4$OH:H$_2$O$_2$:H$_2$O=1 part:1:5 (by volume)) 0.5 ppb of Fe labelled with $^{59}$Fe. Subsequently, this test wafer was drawn up, and rinsed with pure water for 10 minutes, followed by drying to obtain a harmful-element adsorbed sample.

An imaging plate was exposed to radiation in the same manner as in Example 1 except that the harmful-element adsorbed sample used therein was replaced with the harmful-element adsorbed sample of the present Example. The radioactivity intensity distribution pattern of the harmful-element adsorbed sample, recorded in the imaging plate thus exposed, was read on the imaging analyzer BAS2000. Then the $^{59}$Fe densities in the ion-implanted area and the non-implanted area were determined by comparing PSL measured using the imaging analyzer BAS2000 with PSL of the standard sample having a known $^{59}$Fe density. As the result, the $^{59}$Fe density in the ion-implanted area was (7 to 10)×10$^{11}$ atoms/cm$^2$, whereas the $^{59}$Fe density in the non-implanted area was about (2 to 4)×10$^{11}$ atoms/cm$^2$. The defects of metal adsorption prohibiting type are presumed to have occurred in the test wafer used in the present Example.

Example 10

A silicon wafer having swirl defects, which are harmful crystal defects occurring when single-crystal silicon is grown, was prepared. This silicon wafer was heated at 1,000° C. for 8 hours in an oxidizing atmosphere. Then, the oxide film thus produced on the silicon wafer surface was removed with hydrofluoric acid to obtain a test wafer. An imaging plate was exposed to radiation in the same manner as in Example 8 except that the test wafer used therein was replaced with the test wafer prepared in the present Example, and the image thereby formed was observed. As the result, spiral irregular $^{64}$Cu adsorbed areas were clearly seen in the image. Thus, it has become clear that according to the present invention the potential crystal defects present in the vicinity of the surface of a silicon wafer can be examined by actualizing them by such heat treatment.

What is claimed is:

1. A method of examining surface defects of silicon wafer surfaces, comprising;

(A) preparing a semiconductor treating solution containing an impurity element harmful in the process of manufacturing semiconductors; the impurity elements having been labelled with a radioactive isotope;

(B) bringing a silicon wafer whose surface is laid bare, into contact with the semiconductor treating solution to obtain a harmful-element adsorbed wafer on which the labelled impurity element has been adsorbed;

(C) recording in a photostimulable phosphor layer a data of radioactivity intensity distribution present in the surface of the harmful-element adsorbed wafer; the pattern being recorded as a latent image; and (D) reading as a visual image the data of radioactivity intensity distribution recorded in the photostimulable phosphor layer, to observe the radioactivity intensity distribution shown on the image, whereby the distribution of the surface defects being detected.

2. The method according to claim 1, wherein said radioactive isotope used in the step (A) is selected from the group consisting of $^{64}$Cu, $^{61}$Cu, $^{59}$Fe, $^{57}$Ni, $^{22}$Na, $^{24}$Na, $^{45}$Ca, $^{198}$Au and $^{18}$F.

3. The method according to claim 1, wherein said semiconductor treating solution used in the step (A) is an ammonia/hydrogen peroxide cleaner (SC-1), a hydrochloric acid/hydrogen peroxide cleaner (SC-2) or a treating solution containing hydrofluoric acid.

4. The method according to claim 1, wherein the step (C) is carried out after the harmful-element adsorbed wafer has been obtained in the step (B) and then subjected to a cleaning treatment to remove at least 80% of said labelled impurity element adsorbed on the harmful-element adsorbed wafer.

5. The method according to claim 4, wherein a cleaning fluid used in said cleaning treatment is an ammonia/hydrogen peroxide cleaner (SC-1) or a hydrochloric acid/hydrogen peroxide cleaner (SC-2).

6. The method according to claim 1, wherein the silicon wafer used in the step (B) is a starting or processed wafer for a silicon device manufacturing, and having been subjected to a heat treatment.

7. The method according to claim 1, wherein the step (D) further comprises comparing the radioactivity intensity in an area having many crystal defects and the radioactivity intensity in an area having less crystal defects.

8. The method according to claim 1, wherein the silicon wafer used in the step (B) has been contaminated with an organic matter, whereby the distribution of the organic matter as well as the distribution of the crystal defects are detected.

9. The method according to claim 1, wherein the surface defects are crystal defects in the surface of the silicon wafer, surface states formed by contamination with impurities or the both thereof.

* * * * *